United States Patent [19]

Karl et al.

[11] 4,390,712

[45] Jun. 28, 1983

[54] AQUEOUS SOLUTION OF CATIONIC ORGANOSILICON COMPOUNDS AND PROCESS FOR THE PRODUCTION OF THE SOLUTIONS

[75] Inventors: Alfons Karl, Hanau; Wolfgang Buder, Rodenbach; Peter Kleinschmit, Hanau, all of Fed. Rep. of Germany

[73] Assignee: Degussa AG, Frankfurt, Fed. Rep. of Germany

[21] Appl. No.: 298,251

[22] Filed: Aug. 31, 1981

[30] Foreign Application Priority Data

Dec. 19, 1980 [DE] Fed. Rep. of Germany ....... 3047994

[51] Int. Cl.$^3$ ............................................. C07F 7/10
[52] U.S. Cl. ................................ 556/413; 260/239 B; 260/239 A; 544/53; 544/56; 544/170; 544/3; 544/106; 548/146; 548/206; 548/300; 548/335; 548/347; 548/406; 546/14
[58] Field of Search ......................... 546/14; 556/413; 260/326.8, 239 B, 313.1; 544/53, 56, 170; 548/146, 206, 300

[56] References Cited

U.S. PATENT DOCUMENTS

| | | | |
|---|---|---|---|
| 3,557,178 | 1/1971 | Gölitz et al. | 556/413 |
| 3,580,920 | 5/1971 | Culpepper | 546/14 |
| 3,661,963 | 5/1972 | Pepe et al. | 546/14 X |
| 3,819,675 | 6/1974 | Plueddemann | 556/413 |
| 3,963,726 | 6/1976 | Pepe et al. | 546/14 |
| 4,005,118 | 1/1977 | Heckert et al. | 556/413 |
| 4,005,119 | 1/1977 | Heckert et al. | 556/413 |
| 4,035,411 | 7/1977 | Heckert et al. | 556/413 |
| 4,064,155 | 12/1977 | Speier | 556/413 |

FOREIGN PATENT DOCUMENTS

| | | | |
|---|---|---|---|
| 881654 | 7/1953 | Fed. Rep. of Germany | 556/413 |
| 1262272 | 3/1968 | Fed. Rep. of Germany | 556/413 |
| 2221349 | 5/1972 | Fed. Rep. of Germany | 556/413 |
| 2222997 | 12/1972 | Fed. Rep. of Germany | 556/413 |
| 2229580 | 5/1973 | Fed. Rep. of Germany | 556/413 |
| 2408192 | 9/1974 | Fed. Rep. of Germany | 556/413 |
| 2648240 | 6/1977 | Fed. Rep. of Germany | 556/413 |
| 6517163 | 7/1966 | Netherlands | 556/413 |
| 686068 | 1/1953 | United Kingdom | 556/413 |
| 882067 | 11/1961 | United Kingdom | 556/413 |
| 1306992 | 3/1973 | United Kingdom | |

OTHER PUBLICATIONS

"Eur. J. Med. Chem–Chimica Therapeutica", 14, pp. 399-406, 1979.
Chemical Abstracts, vol. 71, (1974), p. 77187.

*Primary Examiner*—Paul F. Shaver
*Attorney, Agent, or Firm*—Cushman, Darby & Cushman

[57] ABSTRACT

There are prepared aqueous solutions of cationic organosilicon compounds which are produced by reacting an alkoxysilylalkyl halide of the formula $(RO)_{3-n}R^1_n$—Si—$R^2$—X (I) where R is $C_1$ to $C_5$ alkyl, methoxy, ethoxy, phenyl, or $C_5$ to $C_8$ cycloalkyl; $R^1$ is $C_1$ to $C_5$ alkyl, phenyl, tolyl, benzyl, or $C_5$ to $C_8$ cycloalkyl; $R^2$ is a divalent ethylenic double bond free hydrocarbon group having 3 to 8 carbon atoms, n is zero, 1 or 2 and X is chlorine, bromine, or iodine with a tertiary amine of the formula $R^3NR^4R^5$ (II) where $R^3$, $R^4$, and $R^5$ are the same or different and each is an alkyl group or benzyl in which the number of carbon atoms of the alkyl group or the alkyl groups together is up to 30 or $R^4$ and $^5$ together with the nitrogen atom, as well as in a given case a further hetero atom selected from the group consisting of oxygen, nitrogen, and sulfur is a univalent five to eight membered heterocyclic ring having three to seven —$CH_2$— groups in the heterocyclic ring, or $R^5$ is a $C_3$ to $C_{12}$ cycloalkyl group in aqueous medium at a temperature from room temperature (e.g. about 20° C.) to 300° C. at a mole ratio of (I) to (II) between 1:0.8 to 1:1,2 and in a given case under pressure.

15 Claims, No Drawings

AQUEOUS SOLUTION OF CATIONIC ORGANOSILICON COMPOUNDS AND PROCESS FOR THE PRODUCTION OF THE SOLUTIONS

BACKGROUND OF THE INVENTION

The invention is directed to aqueous solutions of organosilicon compounds in the form of cationic silanes and/or siloxanes and to their production.

There are known numerous literature which deal with these types of organosilicon compounds and their production (e.g. German Pat. No. 881654, Netherland published application No. 6517163, German Pat. No. 1262272, German OS No. 2221349, German OS No. 2648240, Heckert U.S. Pat. No. 4,035,411, Heckert U.S. Pat. No. 4,005,118, and Heckert U.S. Pat. No. 4,005,119) as well as their uses such as, e.g. algicides (German OS No. 2222997 and German OS No. 2229580), for improving the dyeability of textile fibers (British Pat. No. 882067) or for preventing the growth of bacteria and fungi, i.e. bactericides and fungicides (German AS No. 2408192 and Eurp. J. Med. Chem-Chemica Therapeutica 1979—14, pages 399-406). The entire disclosure of the above-mentioned patents and other literature is hereby incorporated by reference and relied upon.

In the known processes of production, alkoxysilylalkyl halides are reacted directly with amines, including tertiary amines, thus without using a solvent. On the other hand, if a solvent is used, then there are employed organic solvents such as lower aliphatic alcohols, liquid aliphatic and aromatic hydrocarbons, ketones, and the like.

In German Pat. No. 881654, there is described carrying out the reaction in the absence of water (see for example, patent claim 1). This patent corresponds to British Pat. No. 686068. In the British patent, note page 1, lines 51–65.

According to the Netherlands published patent application No. 6517163, likewise there is employed an organic solvent. It is explained that moisture also must be avoided, page 6, line 23.

According to German Pat. No. 1262272, the synthesis is carried out in the presence of an inert polar solvent such as acetonitrile, dimethyl formamide, benzonitrile, or dimethyl sulfoxide. Water is not mentioned. Similar is true for German OS No. 2221349.

German OS No. 2648240 is directed to the problem of providing a new, industrial process for the production of organosilylamine hydrochlorides. The production from chloroalkylsilanes and primary or secondary amines in the mole ratio of 1 to at least 2 takes place in the presence of a lower aliphatic alcohol. The unreacted amine after the end of the reaction is driven out of the reaction zone. Only after this is the desired aqueous solution of the reaction product produced, whereby the alkoxysilyl groups are subject to hydrolysis. In this way there are obtained especial products which form stabile, concentrated aqueous solutions.

It is stated in the above-cited Heckert U.S. Pat. No. 4,035,411 that the two starting compounds are reacted together either directly, thus without the equivalent of a solvent or in the presence of an inert organic solvent, col. 4, lines 6 to 10. As inert solvent, there is employed 2-butanone or dry hexane. Analogous is true for the syntheses which are disclosed in Heckert U.S. Pat. Nos. 4,005,118 and 4,005,119.

SUMMARY OF THE INVENTION

It has now been found surprisingly that a corresponding synthesis can be carried out in aqueous medium and the new aqueous solution formed has valuable properties. Indications have been found that water acts as a reaction accelerator in the present synthesis. The claimed aqueous solution of cationic organosilicon compounds is produced by the reaction of an alkoxysilylalkyl halide of the formula $(RO)_{3-n}-R_n^1-Si-R^2-X$ (I) where R is $C_1$ to $C_5$ alkyl, methoxymethyl, ethoxyethyl, methoxyethyl phenyl, or $C_5$ to $C_8$ cycloalkyl; $R^1$ is $C_1$ to $C_5$ alkyl, phenyl, tolyl, benzyl, or $C_5$ to $C_8$ cycloalkyl; $R^2$ is a divalent ethylenic double bond free hydrocarbon group having 3 to 8 carbon atoms, e.g. alkylene of 3 to 8 carbon atoms, n is zero, 1 or 2, and X is chlorine, bromine, or iodine with a tertiary amine of the formula $R^3NR^4R^5$ (II) where $R^3$, $R^4$, and $R^5$ are the same or different and each is an alkyl group or benzyl in which the number of carbon atoms of the alkyl group or the alkyl groups together is up to 30 or $R^4$ and $^5$ together with the nitrogen atom, as well as in a given case a further hetero atom selected from the group consisting of oxygen, nitrogen, and sulfur is a univalent five to eight membered heterocyclic ring having three to seven $-CH_2-$ groups in the heterocyclic ring, or $R^5$ is a $C_3$ to $C_{12}$ cycloalkyl group in aqueous medium at a temperature from room temperature (e.g. about 20° C.) to 300° C. at a mole ratio of (I) to (II) between 1:0.8 to 1:1,2 and in a given case under pressure.

The symbol $R^2$ includes as the bridging member not only branched and unbranched aliphatic divalent hydrocarbon groups of the type $C_nH_{2n}$ (n is 3 to 8), but also in a given case substituted phenyl groups as, for example, those of the formulae $-CH_2-Ph-$, $-Ch_2-Ph-CH_2-$, $-Ph(CH_3)-$, $-Ph(CH_3)_2-$, and $-Ph(C_2H_5)-$ (Ph=Phenyl).

As amines of formula II, there are also suited so-called cyclic amines wherein the nitrogen atom, together with the groups $R^4$ and $R^5$, can form a heterocyclic ring, which in a given case can have a further heteroatom (nitrogen, oxygen, or sulfur). The carbon of the heterocyclic ring has the form of $-CH_2-$ groups and includes 3 to 7 of these groups. Preferably $R^3$, $R^4$, and $R^5$ are alkyl groups beginning with methyl, ethyl, etc. which can be the same or different. The sum of the carbon atoms of the alkyl groups amounts to up to about 30 carbon atoms.

With long chain alkyl groups (from about 10 carbon atoms) there is limited by manufacture only one such group on the nitrogen atom of the amine, the remaining alkyl groups are short chain (up to about 9 carbon atoms).

There is also claimed the process for the production of the reaction products of alkoxysilylalkyl halides of the above-mentioned formula (I) and tertiary amines of the mentioned formula (II) which is characterized by reacting in aqueous medium at a temperature from room temperature (about 20° C.) to 300° C. at a mole ratio of (I) to (II) between 1:0.8 and 1:1.2 and in a given case using pressure.

It is particularly suitable and tied to advantages to carry out the reaction at a temperature from reflux temperature up to 200° C. at a molar ratio of the above-mentioned compound (I) to the mentioned compound (II) of 1:1 with a deviation of ±5% and in a given case under pressure up to about 200 bar. Preferably, there is employed normal pressure (atmospheric pressure) as well as in a given case pressures of 1 to 25 bar. The reaction time generally dependent on the reaction temperature is from 15 minutes to several hours but can be up to about 70 hours or the corresponding days.

The content of cationic organosilicon compounds in the aqueous solution of the invention can vary between 0.01 and about 95 weight percent according to the intended purpose of use and depending on the starting compounds or on the properties of the reaction products formed, especially their solubilities. It goes without saying the concentrated solutions formed can be diluted to a desired content of organosilicon compounds.

In regard to the mole ratios, preferably there is established a mole ratio of the mentioned starting compounds (I) to (II) of 1:1. An excess or also a deficiency of tertiary amine within the stated limits is possible. An excess of amine is particularly suitable if there is sought a pH of the reaction mixture above 7 or if it is advantageous for the course of the synthesis. Excess amine can be removed, e.g., after ending the synthesis by blowing air into the reaction vessel, as is the case particularly in employing excess trimethylamine. To attain a pH below 7 or to partially keep the —C—X function in the reaction product, there can be used a deficiency of amine.

As starting compound for the synthesis of the invention, there can be used the following silanes and amines for example:

2-iodiosopropyltris(methoxyethoxy)silane, 2-chloroisopropyltris(methoxyethoxy)silane, 3-chloropropyltrimethoxy-, -triethoxy- and tripropoxysilane, 3-iodopropyldimethylethoxysilane, 3-chloropropylcyclohexyldiethoxysilane, 3-bromopropyldiethylcyclopentoxysilane, 3-chloropropylcyclopentyldimethoxysilane, 3-iodopropyltriethoxysilane, 3-chloroisobutyltrimethoxysilane, 3-chloroisobutyltriethoxysilane, 3-bromoisobutyltrimethoxysilane, 3-chloroisobutylbis(ethoxyethoxy)methylsilane, 4-bromo-n-butyltriethoxysilane, 4-chloro-n-butyldiethoxycyclopentylsilane, 4-iodo-3-methylbutyldimethoxyphenylsilane, 5-chloro-n-pentyltri-n-butoxysilane, 5-bromo-n-pentyltriethoxysilane, 4-bromo-3-methylbutyldimethoxyphenylsilane, 5-bromo-n-pentyltri-n-butoxysilane, 5-chloro-n-pentyltriethoxysilane, 5-iodo-4-methylpentyltris(methoxymethoxy)silane, 4-chloro-n-hexylethoxydimethylsilane, 6-bromo-n-hexylpropyldipropoxysilane, 6-iodo-n-hexyldi-n-butoxyethylsilane, 6-chloro-n-hexyldiethoxyethylsilane, 7-chloro-n-heptyltriethoxysilane, 7-chloro-n-heptyldimethoxycycloheptylsilane, 7-bromo-n-heptyldiethoxycyclooctylsilane, 8-chloro-n-octyltriethoxysilane, 8-bromo-n-octyldimethylcyclohexoxysilane, 8-iodo-n-octylcyclooctoxydimethylsilane, 3-chloropropyldiethoxyphenylsilane, 3-chloropropylmethoxyethoxybenzylsilane, 3-bromopropyldimethoxybenzylsilane, 3-iodopropyldimethoxy-p-tolylsilane, p-chlorophenyltrimethoxysilane, p-chlorobenzyltriethoxysilane, p-chloromethyl-phenyl-trimethoxysilane, 3-chloropropyltriamyloxysilane, 8-bromooctylamyldimethoxysilane, 3-chloropropyldimethoxycyclopentoxysilane, and 3-chloropropyldimethoxyamylsilane.

Usable tertiary amines include among others trimethylamine, triethylamine, triisopropylamine, tri-n-propylamine, tribenzylamine, dimethylethylamine, dimethyl-n-butylamine, dimethyl-n-hexylamine, diethyl-n-octylamine, dimethyldodecylamine, dimethylpentadecylamine, diethyloctadecylamine, dimethylheptadecylamine, diethyltetradecylamine, dimethylhexacosylamine, methylethylisopropylamine, methylethylbenzylamine, diethyldecylamine, methyldipentylamine, methylethylheptylamine, methylethylnonylamine, cyclopropyldimethylamine, cyclobutyldiethylamine, cyclopentyldi-n-propylamine, cyclohexyldimethylamine, cyclohexyldiethylamine, cyclohexylmethylethylamine, cycloheptyldimethylamine, cyclooctyldiethylamine, cyclohexyldioctylamine, cyclononyldimethylamine, cyclodecyldiethylamine, cycloundecyldimethylamine, cyclododecyldiethylamine, N-methylpyrrolidine, (=N-methylazolidine in accordance with IUPAC rules), N-ethylpyrrolidine, N-isopropylpyrrolidine, N-benzylpyrrolidine, N-methylpiperidine, N-ethylpiperidine, N-n-propylpiperidine, N-benzylpiperidine, N-methylmorpholine (=4-methylmorpholine or 4-methyltetrahydro-1,4-oxazine), N-ethylmorpholine, N-n-butylmorpholine, N-benzylmorpholine, N-methylimidazolidine, N-ethylimidazolidine, N-n-pentylimidazolidine, N-benzylimidazolidine, N-methylpiperazine, N-ethylpiperazine, N-isopropylpiperazine, N-benzylpiperazine, N-methylthiazolidine, N-ethylthiazolidine, N-methyloxazolidine, N-methyltetrahydro-1,4-thiazine, N-ethyltetrahydro-1,4-thiazine, N-benzyltetrahydro-1,4-thiazine, N-methylperhydroazepine, N-methylhexamethylenimine, N-ethylperhydroazepine, N-benzylperhydroazepine, N-methylperhydroocine (=N-methylheptamethylenimine), N-isopropylperhydroocine, N-benzylperhydroocine, N-ethyltetramethylenimine, N-methylpentamethylenimine, N-ethylpentamethylenimine, and N-benzylpentamethylenimine.

In connection with the present invention, "in aqueous medium" means that the synthesis preferably is carried out with water only but in many cases water is also suitably used with customary organic liquids completely miscible with water under the reaction conditions in which case the upper limit of the portion or organic liquid in the mixture employed is 90 weight percent, preferably the upper limit is 60 weight percent. After the end of the reaction, the portion of organic liquid generally is still further increased by the hydrolysis of the alkoxy groups of the silane employed. As organic liquids, there first come into question lower aliphatic monoalcohols, e.g. alkanols having 1 to 4 carbon atoms thus methanol, ethanol, n-propanol, isopropanol, and the butanols e.g. n-butanol, t-butanol (tert. butyl alcohol) and higher alcohols such as the pentanols and hexanols, etc.; furthermore, there can be used methoxyethanol, ethoxyethanol, acetone, tetrahydrofuran, N,N-dimethyl formamide, N-methylpyrrolidone, nitromethane, and dioxane. For example, there are usable water-alcohol mixtures if long chain silanes and/or long chain amines are employed.

Since to carry out the synthesis there are employed compounds having alkoxysilyl groups at, least partially these groups also react in aqueous solution with splitting off of alcohols and formation of siloxanes. Thus, depending on the properties of the starting compounds and the process conditions, there are formed siloxanes or mixtures of siloxanes and silanes. Thus, it is known that the alkoxy groups are more easily split off hydrolytically the shorter the alkyl chain.

Since the synthesis according to the invention is a time reaction whereby an ammonium salt is formed, the end of the reaction is determined in a particularly suitable manner by gravimetric analysis of the halide content (Hal—). Thus, if this halide content determined, for example, through titration with silver nitrate, with increasing reaction time still increases, then the reaction is not yet ended. If the halide content, for example, determined as Cl— reaches or nearly reaches the calculated final value or nearly the final value, then the reaction is practically finished. Thereby, it must be guaranteed that the analytically determined value, with correct selection of the analytical method, does not include the non-ionic halogen content (still present at the beginning) but only includes the actual anionic halogen content.

The aqueous solutions of the cationic organosilicon compounds of the invention, whether siloxane or mixture of siloxanes and silanes find direct use, e.g. for the coating of inorganic oxide carriers or as flotation aids or flotation agents for ores, especially ores of oxide nature, such as e.g. have hydroxyl groups on the surface or they can be employed as intermediate products to carry out further syntheses. Of course, the cationic organosilicon compounds can be isolated and used further.

Unless otherwise indicated, all parts and percents are by weight.

The compositions can comprise, consist essentially of, or consist of the stated materials; and the process can comprise, consist essentially of, or consist of the steps set forth.

The following examples illustrate the invention in more detail but are not limiting in nature.

DETAILED DESCRIPTION cl Example 1

1.20 kg (5.00 moles) of 3-chloropropyltriethoxysilane (CIPTES) and 985.2 grams of a 30 weight percent aqueous trimethylamine solution (corresponding to 5.00 moles of trimethylamine) were heated in a 5 liter steel autoclave for 3½ hours at 120° C. There was obtained a clear, colorless solution of around 68.5 weight percent content of cationic reaction product whose average chloride content Cl— was determined as 8.19 weight percent compared to the calculated 8.10 weight percent. The NMR-$C^{13}$ analysis (in water with $d_8$-dioxane as standard) gave a measured value $\delta$(—$CH_2$—$N^{\oplus}Me_3$) of 53.8 ppm [the value $\delta$(—$CH_2$—$N^{\oplus}Me_3$) represents the chemical displacement of the methylene group which carry the ammonium group, whereby Me signifies methyl].

Example 2

15 liters of aqueous 45 weight percent trimethylamine solution (=99.35 moles) and 23.92 kg of CIPTES were heated for two hours at 130° C. in a 45 liter internally enamelled pressure container under the autogenous pressure of the reaction mixture. There was formed a clear, only slightly colored solution of the reaction product having the partial formula $\geqslant$Si($CH_2$)$_3$—$N^+$($CH_3$)$_3$Cl$^-$ having a content of cationic reaction product of about 80 weight percent. The analytically determined chloride content (Cl—) was 9.41 weight percent (calculated chloride content 9.46 weight percent).

Example 3

There were heated for five hours at 120° C. 1.20 kg (5.00 moles) of CIPTES, 506 grams (5.00 moles) of triethylamine, and 732.8 grams of water in a 5 liter steel autoclave. The clear, colorless solution formed contained around 70 weight percent of a cationic reaction product with the grouping $\geqslant$Si—($CH_2$)$_3$—$N^+$($C_2H_5$)$_3$Cl$^-$. The analytically determined chloride content was 7.12 weight percent (calculated 7.26 weight percent).

Example 4

664.5 grams of 3-iodopropyltriethoxysilane and 394.1 grams of a 30 weight percent aqueous solution of trimethylamine (containing 118.2 grams=2.00 moles of the amine) were heated for three hours under reflux and normal pressure. There formed a clear, colorless solution of a cationic reaction product having the grouping $\geqslant$Si—($CH_2$)$_3$—$N^+$($CH_3$)$_3$I$^-$, which contained about 73.9 weight percent of the reaction product. The iodide content was determined analytically as 23.72 weight percent (calculated 23.98 weight percent).

Example 5

There were heated under reflux for 2½ hours in a 2 liter capacity glass flask equipped with a thermometer, stirrer, and reflux condenser 664.5 grams of 3-iodopropyltriethoxysilane, 202.4 grams of triethylamine, and 371.5 grams of water. The reaction product obtained having the grouping $\geqslant$Si—($CH_2$)$_3$—$N^+$($C_2H_5$)$_3$I$^-$ is present in the clear and colorless solution to an extent of about 70 weight percent. The analytically determined iodide content was 20.41 weight percent (calculated 20.49 weight percent).

Example 6

426 grams (2.00 moles) of 3-chloropropyldiethoxymethylsilane and 544 grams of water were present in a 2 liter steel autoclave. Then there were added 148 grams (around 2.50 moles) of trimethylamine. The reaction was carried out by heating to 120° C. for three hours under the autogenous pressure of the reaction mixture. Subsequently, the excess amine was removed by blowing air in. In place of air there can be used nitrogen. The clear and colorless solution obtained of around 50 weight percent of the cationic reaction product, having the grouping Si($CH_3$)($CH_2$)$_3$—$N^+$($CH_3$)$_3$Cl$^-$ which had a direct titratable chloride content of 6.45 weight percent (calculated chloride content 6.52 weight percent) can be used directly or after dilution with water and/or ethanol.

Example 7

283 grams (1.00 mole) of 3-chloropropyltris (methoxyethoxy) silane and 1254 grams of water were present in a 2 liter steel autoclave. Then there were added 135 grams (1.00 mole) of benzyldimethylamine and heating carried out under the developed autogenous pressure of the reaction mixture for 12 hours at 130° C. There was obtained a clear almost colorless solution of the cationic reaction product having the grouping $\geqslant$Si—($CH_2$)$_3$—$N^+$($CH_2C_6H_5$)—($CH_3$)$_2$Cl$^-$ have a content of the reaction product of about 25 weight percent. The analytically determined chloride content was 2.03 weight percent (calculated 2.12 weight percent.

Example 8

463.4 grams (2.50 moles) of tri-n-butylamine and 355 grams of a water/ethanol mixture (weight ratio 1:1) were present in a 2 liter steel autoclave then there were added 602 grams (2.50 moles) of CIPTES. The heating was carried out for 60 hours at 130° C. using the autogenous pressure of the reaction mixture. There was formed a slight yellow, clear solution of the reaction producting having the partial formula

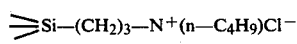

having a content of cationic reaction product of about 75 weight percent. The analytically determined chloride content was 6.10 weight percent (calculated content 6.24 weight percent.

Example 9

602 grams (2.50 moles) of CIPTES, 534 grams (2.50 moles) of dimethyldodecylamine and 284 grams of a water/ethanol mixture in the weight ratio of 2:1 were heated for six hours at 130° C. under the autogenous pressure in a 2 liter steel autoclave. There was obtained a clear, light yellow solution of the reaction product having the partial formula

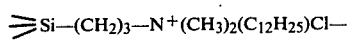

having a content of cationic reaction product of 80 weight percent. The analytically determined chloride content was 6.25 weight percent (calculated content 6.24 weight percent).

For comparison and to prove the significance of water as reaction accelerator there were heated in a glass autoclave for 24 hours at 130° C. 48.2 frams of CIPTES (0.20 mole) and 42.7 grams of dimethyldodecylamine (0.20 mole). According to the Cl— analysis the reaction was only about 60%.

Example 10

602 grams (2.50 moles) of CIPTES, 708.9 grams (2.50 moles) of heptadecyldimethylamine and 1310.9 grams of a water/ethanol mixture (weight ratio 1:1) were heated in a 5 liter steel autoclave for 6 hours at 150° C. There was obtained a light yellow, clear solution of the reaction product having the partial formula

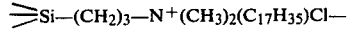

and a content of cationic reaction product of about 50% weight percent. The analytically determined chloride content was 3.25 weight percent (calculated value 3.38 weight percent).

Example 11

616.9 grams (2.50 moles) of p-chloromethylphenyltrimethoxysilane, 253.0 grams (2.50 moles) of triethylamine and 869.9 grams of a water/ethanol mixture in a weight ratio of 1:1 were heated for 5 hours in a 2 liter steel autoclave. There was formed a light yellow solution of the reaction product having the partial formula

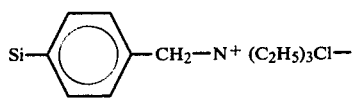

and having a content of cationic reaction product of about 50 weight percent. The analytically determined chloride content was 5.21 weight percent (calculated value 5.09 weight percent).

Example 12

There were present in a 2 liter steel autoclave 202.3 grams (2.00 moles) of N-methylmorpholine and 772.8 grams of water. After addition of 570.5 grams (2.00 moles) of 3-bromopropyltriethoxysilane, the reaction mixture was heated for 2 hours at 130° C. under the autogenous pressure. There was obtained a clear, slightly light yellow solution of the reaction product having the partial formula

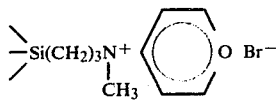

and having a content of cationic reaction product of about 50 weight percent. The analytically determined bromide content was 10.32 weight percent (calculated value 10.34 weight percent).

The determinations of the halide content were carried out potentiometrically (see Jander, Jahr and Knoll "Massanalyse, Theorie und Praxis der klassischen und der elektrochemischen Titrierverfahren," pages 301 to 305, Collection Goschen, Vol. 221 and 221a, Gerlay Walter de Gruyter & Co., Berlin (1969). Further possibilities of determination see also pages 222 to 228.

The entire disclosure of the German priority application No. P3047994.8 is hereby incorporated by reference.

What is claimed is:

1. A process of preparing an aqueous solution of a cationic organosilicon compound, comprising reacting an alkoxysilylalkyl halide of the formula $(RO)_{3-n}R^1_n$—Si—$R^2$—X (I) where R is $C_1$ to $C_5$ alkyl, methoxymethyl, ethoxyethyl, methoxyethyl, or $C_5$ to $C_8$ cycloalkyl, $R^1$ is $C_1$ to $C_5$ alkyl, phenyl, tolyl, benzyl, or $C_5$ to $C_8$ cycloalkyl; $R^2$ is a divalent ethylenic double bond free hydrocarbon group having 3 to 8 carbon atoms, n is zero, 1 or 2 and X is chlorine, bromine, or iodine with a tertiary amine of the formula $R^3NR^4R^5$ (II) where $R^3$, $R^4$, and $R^5$ each is an alkyl group or benzyl in which the number of carbon atoms of the alkyl group or the alkyl groups together is up to 30 or $R^4$ and $R^5$ together with the nitrogen atom or together with the nitrogen atom together with a further hetero atom selected from the group consisting of oxygen, nitrogen, and sulfur is a univalent five to eight membered heterocyclic ring having three to seven —$CH_2$— groups in the heterocyclic ring, or $R^5$ is a $C_3$ to $C_{12}$ cycloalkyl group in aqueous medium at a temperature from room temperature to 300° C. at a mole ratio of (I) to (II) between 1:0.8 to 1:1.2.

2. A process according to claim 1 where $R^2$ is an alkylene group.

3. A process according to claim 2 wherein n is zero.

4. A process according to claim 3 wherein (I) is 3-chloropropyltriethoxysilane.

5. A process according to claim 4 wherein $R^3$ and $R^4$ are alkyl groups of 1 to 4 carbon atoms and $R^5$ is alkyl.

6. A process according to claim 1 where when $R^4$ and $R^5$ for a heterocyclic ring, it is pyrrolidine, piperidine, morpholine, piperazine, thiazolidine, oxazolidine, thiazine, perhydroacepine, or hexamethylenimine ring.

7. A process according to claim 1 wherein $R^4$ and $R^5$ are joined to form a morpholine ring.

8. A process according to claim 1 where $R^2$ is alkylenephenyl wherein the alkylene group has 1 to 2 carbon atoms.

9. A process according to claim 1 wherein water is the sole solvent.

10. A process according to claim 1 wherein the solvent is a mixture of water and a water soluble organic solvent which is a water soluble alkanol, water soluble alkoxyalkanol, water soluble ketone, tetrahydrofurane, N,N-dimethyl formamide, N-methyl pyrrolidone, nitromethane or dioxane, the water being at least 10 weight percent of the total solvent.

11. A process according to claim 10 wherein the water is at least 40 weight percent of the total solvent.

12. A process according to claim 1 wherein the temperature is from reflux temperature to 200° C. and the mole ratio of the compound of formula (I) to the compound of formula (II) is 1:1±5%.

13. A process according to claim 12 wherein the pressure is atmospheric pressure.

14. A process according to claim 12 wherein the reaction is carried out in a closed container at autogenous pressure up to 200 bar.

15. A process according to claim 14 wherein the pressure is 1 to 25 bar.

* * * * *